United States Patent
Si et al.

(10) Patent No.: US 8,348,831 B2
(45) Date of Patent: Jan. 8, 2013

(54) DEVICE AND METHOD FOR COMPUTER SIMULATED MARKING TARGETING BIOPSY

(75) Inventors: Jianmin Si, Hangzhou (CN); Jiquan Liu, Hangzhou (CN); Jingyi Feng, Hangzhou (CN); Shujie Chen, Hangzhou (CN); Liangjing Wang, Hangzhou (CN); Jiaguo Wu, Hangzhou (CN); Yi Lv, Hangzhou (CN)

(73) Assignees: Zhejiang University, Hangzhou (CN); Hangzhou Botong Gastroenteropathy Treatment Technology Co., Ltd., Hangzhou (CN)

( * ) Notice: Subject to any disclaimer, the term of this patent is extended or adjusted under 35 U.S.C. 154(b) by 459 days.

(21) Appl. No.: 12/638,955

(22) Filed: Dec. 15, 2009

(65) Prior Publication Data

US 2011/0144432 A1     Jun. 16, 2011

(51) Int. Cl.
*A61B 5/05* (2006.01)
(52) U.S. Cl. ......... 600/117; 600/424
(58) Field of Classification Search ......... 600/101–117, 600/424; 73/866.5
See application file for complete search history.

(56) References Cited

U.S. PATENT DOCUMENTS

| | | | | |
|---|---|---|---|---|
| 4,710,876 A * | 12/1987 | Cline et al. | | 345/423 |
| 5,307,072 A * | 4/1994 | Jones, Jr. | | 342/147 |
| 5,611,025 A * | 3/1997 | Lorensen et al. | | 345/419 |
| 5,800,352 A * | 9/1998 | Ferre et al. | | 600/407 |
| 5,967,980 A * | 10/1999 | Ferre et al. | | 600/424 |
| 6,591,130 B2 * | 7/2003 | Shahidi | | 600/424 |
| 6,980,921 B2 * | 12/2005 | Anderson et al. | | 702/150 |
| 7,542,869 B2 * | 6/2009 | Gandelsman et al. | | 702/152 |
| 7,901,348 B2 * | 3/2011 | Soper et al. | | 600/117 |
| 8,145,292 B2 * | 3/2012 | Vining | | 600/407 |
| 2002/0193687 A1 * | 12/2002 | Vining et al. | | 600/425 |
| 2003/0139895 A1 * | 7/2003 | Lescourret | | 702/150 |
| 2004/0070582 A1 * | 4/2004 | Smith et al. | | 345/419 |
| 2004/0105573 A1 * | 6/2004 | Neumann et al. | | 382/103 |
| 2004/0107070 A1 * | 6/2004 | Anderson et al. | | 702/150 |
| 2010/0284594 A1 * | 11/2010 | Hohne et al. | | 382/131 |
| 2011/0044521 A1 * | 2/2011 | Tewfik et al. | | 382/131 |
| 2011/0082366 A1 * | 4/2011 | Scully et al. | | 600/424 |
| 2011/0128352 A1 * | 6/2011 | Higgins et al. | | 348/46 |
| 2012/0059248 A1 * | 3/2012 | Holsing et al. | | 600/424 |

OTHER PUBLICATIONS

Virtual Endoscopy: development and evaluation using the Visible Human Datasets, R.A. Robb, Mayo Foundation, Biomedical Imaging Resource, Dec. 6, 1999.*
A Computer Simulated Biopsy Marking System for Gastroscopy, Deyu Sun, Wei Wu, Yi Lu, Jiquan Liu, Huilong Duan, College of Biomedical Engineering & Instrument Science of Zhejiang University, Hangzhou, Zhejiang, IEEEXplore, Jul. 23, 2010.*
Virtual Scopy with Multidector CT, Surg Cdr IK Indrajit, Surg Capt JD Souza, Surg Cdr R Pant, Surg Cdr PC Handle, Medical Journal Armed Forces India, vol. 62, Issue 1, pp. 60-63, Jan. 2006.*

* cited by examiner

Primary Examiner — Clayton E Laballe
Assistant Examiner — Kevin Butler
(74) Attorney, Agent, or Firm — Matthias Scholl P.C.; Matthias Scholl

(57) ABSTRACT

A device for Computer Simulated Marking Targeting Biopsy (CSMTB) has at least a space locator, and a main control module, including a surface model sub-module, a positioning sub-module, a tracking sub-module, a virtual endoscope sub-module, and a marking targeting biopsy sub-module. The device accurately detects minimal gastric lesions, and reduces pain to patients and thus decreases the workload of a doctor.

9 Claims, 5 Drawing Sheets

DEVICE AND METHOD FOR COMPUTER SIMULATED MARKING TARGETING BIOPSY

BACKGROUND OF THE INVENTION

1. Field of the Invention

The invention relates to a device and a method, and more particularly to a device and a method for Computer Simulated Marking Targeting Biopsy (CSMTB).

2. Description of the Related Art

The marking targeting biopsy (MTB) technique has been widely used for detecting gastric lesions. However, there are several problems with the existing MTB technique: firstly, minimal gastric lesions cannot be accurately detected; secondly, since image analysis of gastric lesions has to be done inside a patient's body, the patient has to undergo great pain; finally, detection using the MTB technique relies on movement of a probe of a gastroscope, which brings great pain to the patient, and increases workload of a doctor.

SUMMARY OF THE INVENTION

In view of the above-described problem, it is one objective of the invention to provide a device for Computer Simulated Marking Targeting Biopsy (CSMTB) that is capable of accurately detecting minimal gastric lesions, and bringing slight pain to a patient and thus decreasing workload of a doctor.

It is another objective of the invention to provide a method for Computer Simulated Marking Targeting Biopsy (CSMTB) that is capable of accurately detecting minimal gastric lesions, and bringing slight pain to a patient and thus decreasing workload of a doctor.

To achieve the above objectives, in accordance with one embodiment of the invention, provided is a device for Computer Simulated Marking Targeting Biopsy (CSMTB), comprising a space locator, and a main control module, comprising a surface model sub-module, a positioning sub-module, a tracking sub-module, a virtual endoscope sub-module, and a marking targeting biopsy sub-module, wherein the space locator is connected to the main control module, and operates to obtain position and orientation information of a probe of a gastroscope, the surface model sub-module operates to construct and store a 3D surface model of inner wall of a stomach, the positioning sub-module operates to collect and store a signal from the space locator, the tracking sub-module operates to read data in the positioning sub-module and to adjust a position and an orientation of an endoscopic viewpoint in the 3D surface model of the inner wall of the stomach, the virtual endoscope sub-module operates to endoscopically image and display the 3D surface model of the inner wall of the stomach according to the position and the orientation of the endoscopic viewpoint, and the marking targeting biopsy sub-module operates to record the position and the orientation of the endoscopic viewpoint, to mark the position and the orientation of the endoscopic viewpoint in the 3D surface model of inner wall of a stomach, and to navigate and display the endoscopic viewpoint during endoscopic imaging of the 3D surface model of the inner wall of the stomach.

In a class of this embodiment, the space locator comprises a magnetic field transmitter, an electronics unit, a signal preamplifier, and a sensor.

In a class of this embodiment, the electronics unit is connected to the magnetic field transmitter via a parallel interface, and to an output end of the signal preamplifier via a signal line.

In a class of this embodiment, the sensor is connected to an input end of the signal preamplifier, and operates to obtain position and orientation information of the probe of the gastroscope.

In a class of this embodiment, the electronics unit is connected to the main control module.

In accordance with another embodiment of the invention, provided is a method for Computer Simulated Marking Targeting Biopsy (CSMTB), comprising obtaining a slice-scan image sequence of a stomach cavity of a patient by a computed tomography equipment, analyzing and performing threshold segmentation on the slice-scan image sequence whereby obtaining a binary image that distinguishes a cavity region of a stomach of the patient from a non-cavity region thereof, extracting an interface between the cavity region and the non-cavity region whereby constructing and rendering a 3D surface model of inner wall of the stomach, obtaining position and orientation information of a probe of a gastroscope via a space locator, adjusting a position and an orientation of an endoscopic viewpoint in the 3D surface model of the inner wall of the stomach according to the position and orientation information of the probe of the gastroscope, endoscopically imaging and displaying the 3D surface model of the inner wall of the stomach according to the position and the orientation of the endoscopic viewpoint, recording the position and the orientation of the endoscopic viewpoint and marking the position and the orientation of the endoscopic viewpoint in the 3D surface model of inner wall of a stomach, and navigating and displaying the endoscopic viewpoint during endoscopic imaging of the 3D surface model of the inner wall of the stomach.

Advantages of the invention comprise:
1. the invention is suitable for long-term reexamination and follow-up since it is capable of detecting minimal gastric lesions and preventing missing lesions.
2. the invention makes it possible for a doctor to perform image analysis of gastric lesions outside a patient's body, which releases pain of the patient.
3. the invention features a navigation function, which effectively reduces time of keeping a probe in a stomach of a patient, and thus releasing pain of the patient and decreasing workload of a doctor.

BRIEF DESCRIPTION OF THE DRAWINGS

The invention is described hereinafter with reference to accompanying drawings, in which.

DETAILED DESCRIPTION OF THE EMBODIMENTS

Figure 1:
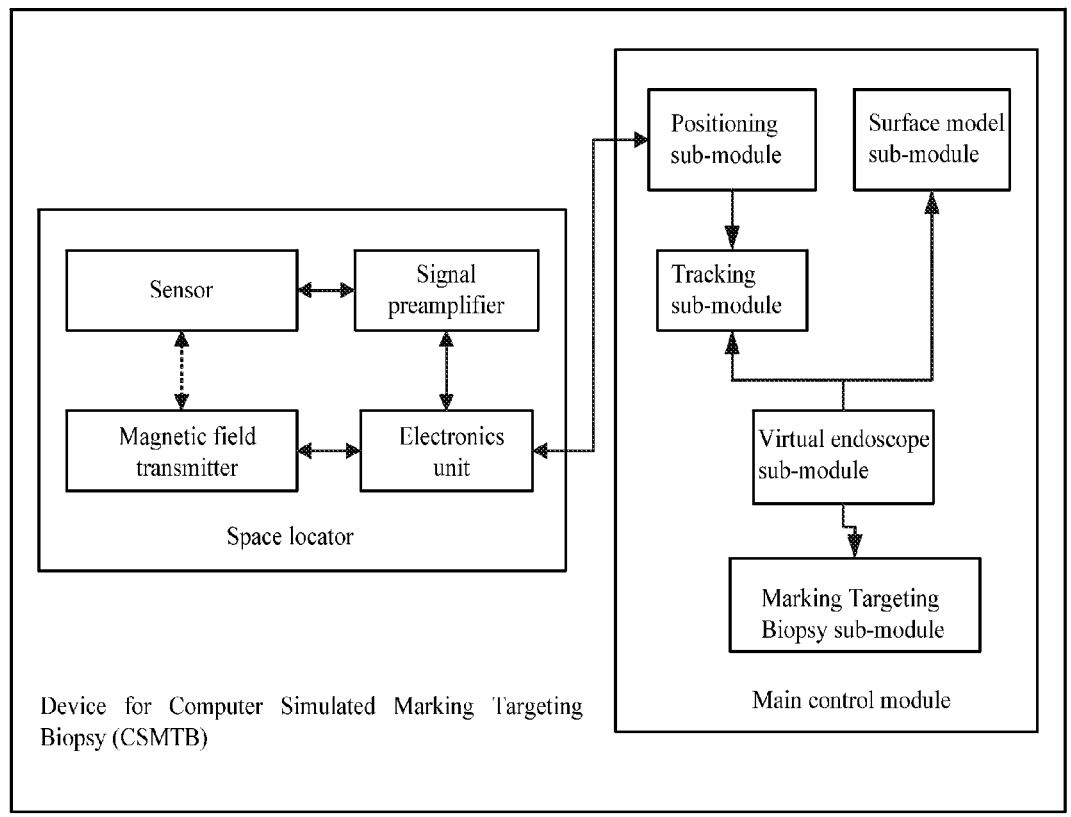
FIG. 1 is a block diagram of a device for Computer Simulated Marking Targeting Biopsy (CSMTB) of an exemplary embodiment of the invention.

As shown in FIG. 1, a device for Computer Simulated Marking Targeting Biopsy (CSMTB) comprises a space locator, and a main control module.

The main control module comprises a surface model sub-module, a positioning sub-module, a tracking sub-module, a virtual endoscope sub-module, and a marking targeting biopsy sub-module.

The space locator is connected to the main control module, and operates to obtain position and orientation information of a probe of a gastroscope.

The surface model sub-module operates to construct and store a 3D surface model of inner wall of a stomach.

The positioning sub-module operates to collect and store a signal from the space locator.

The tracking sub-module operates to read data in the positioning sub-module and to adjust a position and an orientation of an endoscopic viewpoint in the 3D surface model of the inner wall of the stomach.

The virtual endoscope sub-module operates to endoscopically image and display the 3D surface model of the inner wall of the stomach according to the position and the orientation of the endoscopic viewpoint.

The marking targeting biopsy sub-module operates to record the position and the orientation of the endoscopic viewpoint, to mark the position and the orientation of the endoscopic viewpoint in the 3D surface model of inner wall of a stomach, and to navigate and display the endoscopic viewpoint during endoscopic imaging of the 3D surface model of the inner wall of the stomach.

The space locator comprises a magnetic field transmitter, an electronics unit, a signal preamplifier, and a sensor.

The electronics unit is connected to the magnetic field transmitter via a parallel interface, to an output end of the signal preamplifier via a signal line, and to the main control module.

The sensor is connected to an input end of the signal preamplifier, and operates to obtain position and orientation information of the probe of the gastroscope.

Figure 2:
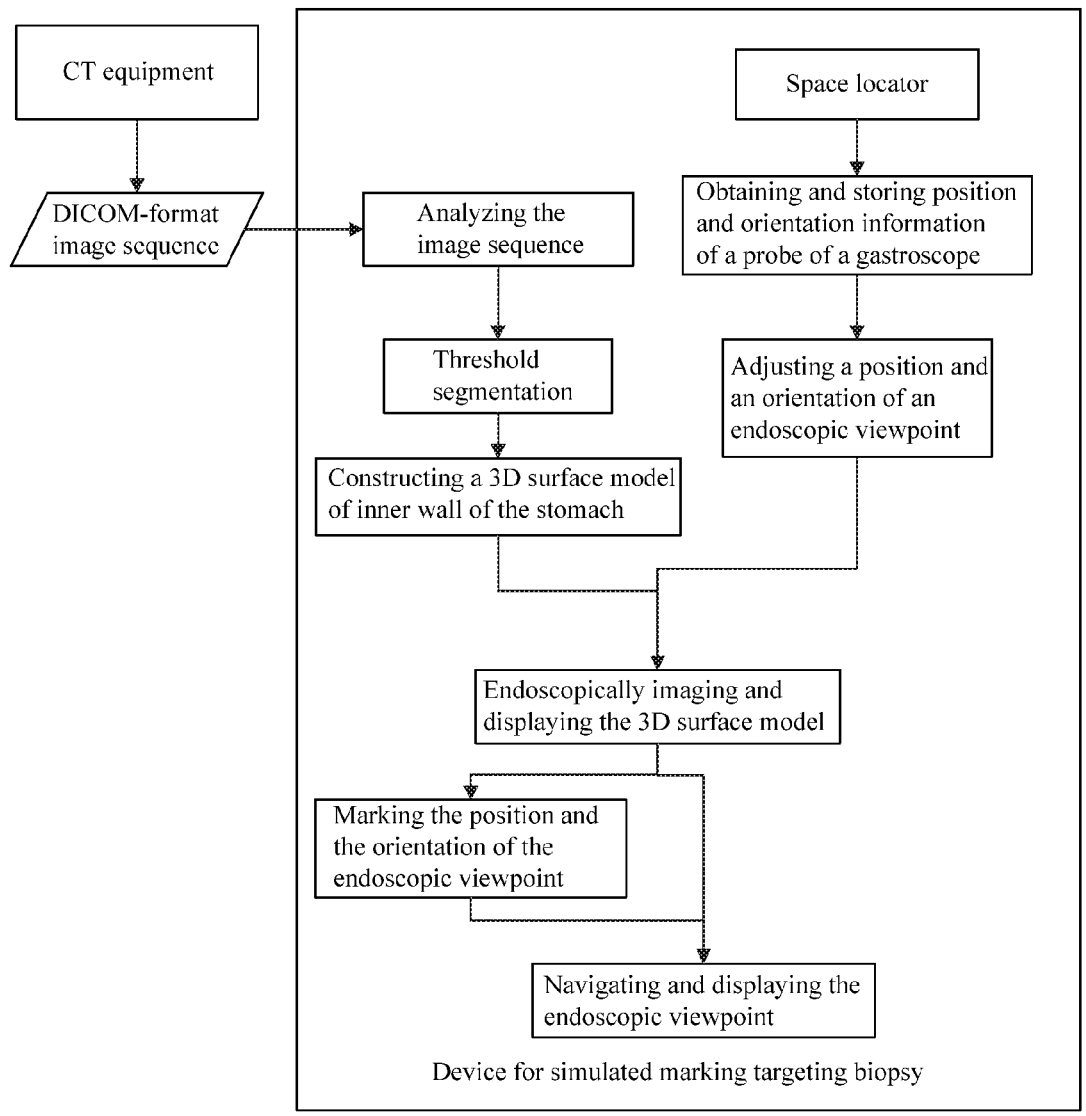
FIG. 2 is a flowchart of a method for Computer Simulated Marking Targeting Biopsy (CSMTB) of another exemplary embodiment of the invention.

As shown in FIG. 2, a method for Computer Simulated Marking Targeting Biopsy (CSMTB) comprises:

1) obtaining a slice-scan image sequence of a stomach cavity of a patient by a computed tomography equipment;

2) analyzing and performing threshold segmentation on the slice-scan image sequence whereby obtaining a binary image that distinguishes a cavity region of a stomach of the patient from a non-cavity region thereof;

3) extracting an interface between the cavity region and the non-cavity region whereby constructing and rendering a 3D surface model of inner wall of the stomach;

4) obtaining position and orientation information of a probe of a gastroscope via a space locator;

5) adjusting a position and an orientation of an endoscopic viewpoint in the 3D surface model of the inner wall of the stomach according to the position and orientation information of the probe of the gastroscope;

6) endoscopically imaging and displaying the 3D surface model of the inner wall of the stomach according to the position and the orientation of the endoscopic viewpoint;

7) recording the position and the orientation of the endoscopic viewpoint and marking the position and the orientation of the endoscopic viewpoint in the 3D surface model of inner wall of a stomach; and 8) navigating and displaying the endoscopic viewpoint during endoscopic imaging of the 3D surface model of the inner wall of the stomach.

In details, firstly a patient's abdomen is plain-scanned via a computed tomography (CT) equipment whereby obtaining a slice-scan image sequence of a stomach cavity. During the plain scan, it is required that an axial direction of a slice-scan space be parallel to a scanning bed, and a position of an origin of the slice-scan space be marked. Then, the slice-scan image sequence is transmitted to the surface model sub-module. In this embodiment, the slice-scan image is Digital Imaging and Communications in Medicine (DICOM) format.

The surface model sub-module analyzes the slice-scan image, maps the slice-scan image to 256 gray levels via a gray window, and displays the slice-scan image in a computer.

During segmentation of the slice-scan image, firstly threshold segmentation is performed on the image according to a required gray-level threshold, segmentation is performed thereon via a region growing method according to any seed point of the cavity specified by a user, and then a binary image that distinguishes a cavity region from a non-cavity region thereof is formed. After that, an interface between the cavity region and the non-cavity region is extracted from the segmented image via a marching cube method, and smoothing and mesh simplification are performed on the interface whereby constructing and rendering a 3D surface model of inner wall of the stomach. Finally, after distributing characteristic coefficients, such as color, photometric properties and so on, to the surface of the model, virtual light is defined for rendering, and the 3D surface model of the inner wall of the stomach is stored in the surface model sub-module.

During operation of the gastroscope, the electronics unit is connected to the main control module. Meanwhile, the sensor of the space locator is wrapped on the probe of the gastroscope via a cavity of the gastroscope, so that a position and an orientation of a probe of sensor are those of the gastroscope. It is required that the sensor is within an image data space of a computed tomography equipment and an effective measurement space of the space locator whereby ensuring correct measurement and reducing possibility of incorrect tracing caused by deviation of the sensor from the effective measurement space.

As the sensor is within the effective measurement space of the space locator, as the position or the orientation of the sensor varies, a DC magnetic field generated by the magnetic field transmitter interacts with the sensor, and real-time and measurable signal variation is generated in the sensor. After being received by the signal preamplifier, the signal variation is received by the electronics unit. At this time, the electronics unit computes and outputs six measured freedom degrees of the sensor in real time, comprising measured values x, y and z on an X axis, a Y axis and a Z axis, a horizontal shift angle a, an elevation angle e, and a twist angle r.

The positioning sub-module controls and communicates with the space locator. In a constant time period specified by the user, the positioning sub-module repeatedly obtains and stores six measured freedom degrees of the sensor.

The tracking sub-module reads the data in the positioning sub-module, and adjusts a position and an orientation of an endoscopic viewpoint in the 3D surface model of the inner wall of the stomach in real time according to the position of the probe of the gastroscope with respect to the space locator and the position of the space locator with respect to the slice-scan space.

The virtual endoscope sub-module endoscopically images and displays the 3D surface model of the inner wall of the stomach according to the position and the orientation of the endoscopic viewpoint output by the tracking sub-module. The virtual endoscope sub-module can operate in two virtual endoscope modes: a track-oriented mode and a user-oriented mode.

In the track-oriented mode, a position of a virtual endoscope sub-module is dependent on results of mobile tracking. The virtual endoscope sub-module provides results of virtual endoscope of the surface model of the inner wall of the stomach according to the position and the orientation of the endoscopic viewpoint obtained via mobile tracking. In the user-oriented mode, the user uses a keyboard to control the position (to move towards or off a view field) and the orientation (ascending, descending, right-turn, and left-turn) of the endoscopic viewpoint, defines view directions of a view of an endoscope according to view directions in a global view, or is capable of defining parameters such as a forward speed and a backward speed of a camera, a twist angle of a virtual camera and so on. In the user-oriented mode, hardware data of the space locator are not obtained, positioning and mobile tracking of the endoscopic viewpoint are performed via an image with three orthogonal sections of a global view angle and slice data.

The marking targeting biopsy sub-module records the position and the orientation of a specific endoscopic viewpoint (an endoscopic viewpoint that needs to be marked), marks the position and the orientation of the endoscopic viewpoint in the 3D surface model of inner wall of a stomach, and navigates and displays the endoscopic viewpoint in the 3D surface model of the inner wall of the stomach.

As a doctor finds a lesion during gastroscopic examination, he or she interactively notifies the marking targeting biopsy sub-module, and the marking targeting biopsy sub-module marks a position of the lesion according to results of mobile tracking of the probe of the gastroscope, whereby facilitating simulated marking of the position of the lesion. After that, as the doctor performs reexamination and follow-up on the patient, the marking targeting biopsy sub-module guides the doctor to find the position of the lesion via navigation according to the position of the probe of the gastroscope and a marked position of the lesion, which improves accuracy of the reexamination, reduces time of the reexamination, alleviates pain to the patient, and decreases workload of the doctor.

The invention integrates functions, such as introduction of medical slice-scan images, mapping of gray windows, displaying of image sequences, image segmentation, surface reconstruction, data acquisition, virtual endoscope, simulated marking biopsy, and so on altogether. The device for Computer Simulated Marking Targeting Biopsy (CSMTB) is capable of outputting an image with three orthogonal sections (a coronal section, a sagittal section, and a cross section) of a global view angle, a view angle of an endoscope, and slice-scan image.

The global view angle draws the 3D surface model of the inner wall of the stomach, the endoscopic viewpoint, a frame of a slice-scan image data space, and the magnetic field transmitter, and enables them to be in appropriate positions. Meanwhile, a user is capable of selecting whether roles of the view field are visible, or the model of the wall of the stomach is transparent.

The view angle of an endoscope makes it possible to virtually endoscope the model.

The image with three orthogonal sections provides a coronal section, a sagittal section, and a cross section of a slice-scan image. In the image, a cross line indicates positions of two sections other than the current one, and a cross is a position of the probe of the gastroscope.

Figure 3:
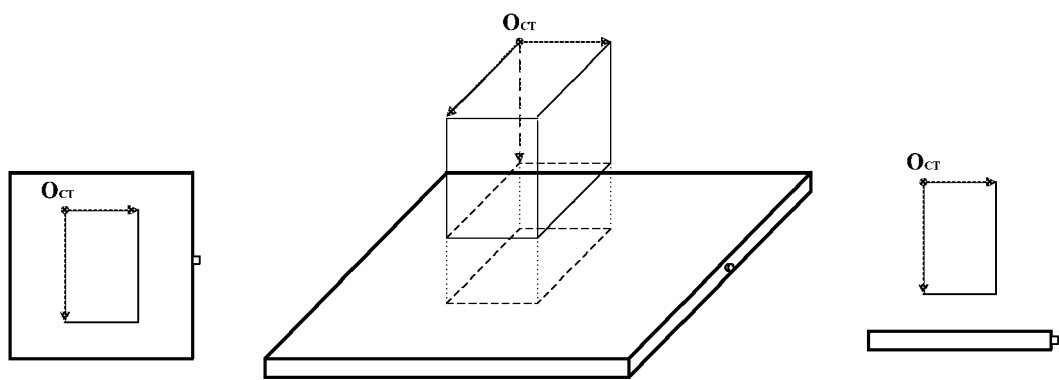
FIG. 3 illustrates positions of an image data space of a computed tomography equipment and a magnetic field transmitter.

As shown in FIG. 3, a left view is a top view, a middle view is a bottom view, and a right view is an axial view.

A slice-scan image data space refers to a 3D space indicated by multiple slice-scan image sequences for reconstruction. A frame formed by solid lines above the magnetic field transmitter indicates the slice-scan image data space, and arrows thereon indicate directions of measuring coordinates.

An origin (OCT) of the space is determined by positions of a patient and a computed tomography equipment, a dimension of the space is determined by scanning parameters of the computed tomography equipment.

For a DICOM-format image, scanning parameters, such as an pixel interval, a fault interval, a position of an origin, a pixel size, and so on, can be analyzed from an image file and directly used. For a non-DICOM-format image, appropriate scanning parameters have to be specified. In this invention, the position of the slice-scan image data space is not dependent on the space locator, but on a position of the patient.

Figure 4:
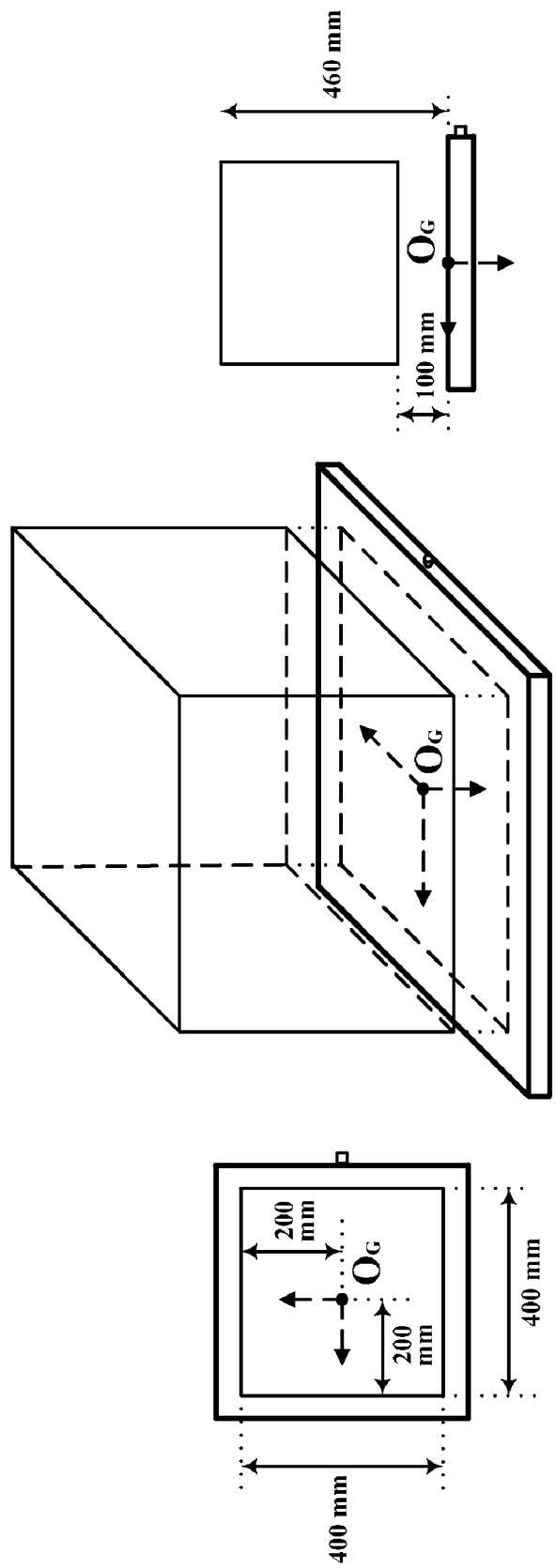
FIG. 4 illustrates positions of an effective measurement space of a space locator and a magnetic field transmitter.

As shown in FIG. 4, a left view is a top view, a middle view is a bottom view, and a right view is an axial view.

An effective measurement space refers to a stable space generated by the space locator and having a low error. The effective measurement space is disposed in a cube right above the magnetic field transmitter. In this embodiment, a dimension of the cube is 400 mm (length)×400 mm (width)×360 mm (height), a distance between the bottom of the cube and the top of the magnetic field transmitter is 100 mm.

A frame formed by solid lines above the magnetic field transmitter indicates the effective measurement space, and arrows thereon indicate directions of measuring coordinates.

An origin (OG) is a center point of an upper surface of the magnetic field transmitter, and a direction thereof is indicated by an arrow.

A dimension of the effective measurement space is a parameter of the magnetic field transmitter that is independent on factors such as the computed tomography equipment, a scanning part, a posture, and a position of a patient, and so on.

Figure 5:
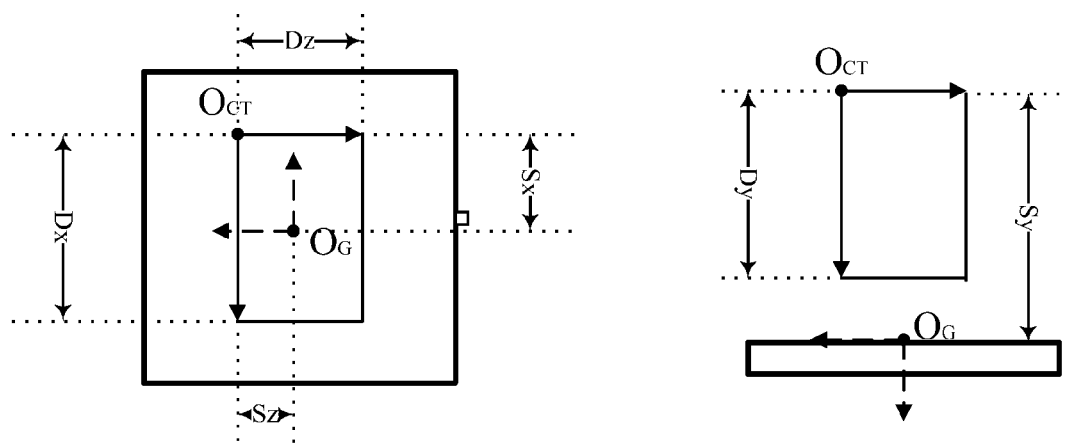
FIG. 5 illustrates positions of an image data space of a computed tomography equipment and an effective measurement space of a space locator.

As shown in FIG. 5, the image data space is a space that reconstructs a surface model of inner wall of a stomach according to a slice-scan image, and a spatial position of the image data space is only dependent on a position of a patient. The effective measuring space is an activity space of the sensor and operates to calculate a relative position of an endoscopic viewpoint, and a spatial position of the effective measuring space is only dependent on a position of the space locator. Therefore, to ensure the relative position of the endoscopic viewpoint in the surface model of the inner wall of the stomach reflects a position of a probe of a gastroscope in the inner wall of the stomach, relative positions of the image data space and the effective measuring space are needed, namely, corresponding sidelines of the image data space and the effective measuring space should be parallel to each other, and values of $S_X$, $S_Y$, and $S_Z$ should be determined (according to $O_{CT}$, $O_G$, $D_X$, $D_Y$, and $D_Z$), then it is possible to draw the relative positions of the endoscopic viewpoint and the surface model of the inner wall of the stomach.

In the tracking sub-module, the endoscopic viewpoint is adjusted in the surface model in real time according to the position and the orientation of the probe in the positioning sub-module. Meanwhile, a cross line is used to locate a position of the probe in a slice-scan image with three orthogonal sections. During simulated marking biopsy, if it is required to control translation of the magnetic field transmitter since space is not enough or mis-positioning occurs, the tracking sub-module allows a user to adjust translation amounts SX, SY, and SZ, whereby making them adapt to variation of hardware and guaranteeing correction of drawing results. A maximum value and a minimum value of a glide bar are calculated according to system parameters whereby ensuring the image data space does not move out of the effective measuring space as the glide bar is adjusted.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for Computer Simulated Marking Targeting Biopsy, comprising
    a space locator; and
    a main control module, comprising
        a surface model sub-module;
        a positioning sub-module;
        a tracking sub-module;
        a virtual endoscope sub-module; and
        a marking targeting biopsy sub-module;
    wherein
    said space locator is connected to said main control module, and operates to obtain position and orientation information of a probe of a gastroscope;
    said surface model sub-module operates to construct and store a 3D surface model of inner wall of a stomach;
    said positioning sub-module operates to collect and store a signal from said space locator;
    said tracking sub-module operates to read data in said positioning sub-module and to adjust a position and an orientation of a virtual endoscopic viewpoint in said 3D surface model of the inner wall of the stomach;
    said virtual endoscope sub-module operates to endoscopically image and display said 3D surface model of the inner wall of the stomach according to the position and the orientation of said virtual endoscopic viewpoint; and
    said marking targeting biopsy sub-module operates to record the position and the orientation of said virtual endoscopic viewpoint, to mark the position and the orientation of said virtual endoscopic viewpoint in said 3D surface model of inner wall of a stomach, to navigate the probe to a position and an orientation in the stomach cavity according to a pre-recorded position and orientation of said virtual endoscopic viewpoint, and to display an endoscopic image of the stomach obtained by the probe during endoscopic imaging of said 3D surface model of the inner wall of the stomach.

2. The device for Computer Simulated Marking Targeting Biopsy of claim 1, wherein said space locator comprises a magnetic field transmitter, an electronics unit, a signal preamplifier, and a sensor.

3. The device for Computer Simulated Marking Targeting Biopsy of claim 2, wherein said electronics unit is connected to said magnetic field transmitter via a parallel interface, and to an output end of said signal preamplifier via a signal line.

4. The device for Computer Simulated Marking Targeting Biopsy of claim 2, wherein said sensor is connected to an input end of said signal preamplifier, and operates to obtain position and orientation information of the probe of the gastroscope.

5. The device for Computer Simulated Marking Targeting Biopsy of claim 2, wherein said electronics unit is connected to said main control module.

6. A method for Computer Simulated Marking Targeting Biopsy, comprising;
    (a) obtaining a slice-scan image sequence of a stomach cavity of a patient by a computed tomography equipment;
    (b) analyzing and performing threshold segmentation on said slice-scan image sequence whereby obtaining a binary image that distinguishes a cavity region of a stomach of the patient from a non-cavity region thereof;
    (c) extracting an interface between said cavity region and said non-cavity region whereby constructing and rendering a 3D surface model of inner wall of the stomach;
    (d) obtaining position and orientation information of a probe of a gastroscope via a space locator;
    (e) adjusting a position and an orientation of a virtual endoscopic viewpoint in said 3D surface model of the inner wall of the stomach according to said position and orientation information of the probe of the gastroscope;
    (f) endoscopically imaging and displaying said 3D surface model of the inner wall of the stomach according to the position and the orientation of said virtual endoscopic viewpoint;
    (g) recording the position and the orientation of said virtual endoscopic viewpoint and marking the position and the orientation of said virtual endoscopic viewpoint in said 3D surface model of inner wall of a stomach resulting in a pre-recorded position and orientation of said virtual endoscopic viewpoint; and
    (h) navigating the probe to a position and an orientation in the stomach cavity according to said pre-recorded position and orientation of said virtual endoscopic viewpoint, and displaying an endoscopic image of the stomach obtained by the probe during endoscopic imaging of said 3D surface model of the inner wall of the stomach.

7. The device of claim 1, wherein said marking targeting biopsy sub-module comprises a data storage unit, said data storage unit is adapted to record position and orientation data of virtual endoscopic viewpoints, and said marking targeting biopsy sub-module is adapted to write the data to and read the data from said data storage unit.

8. The device of claim 7, wherein:
    when said marking targeting biopsy sub-module is operated to mark a position and an orientation of a virtual endoscopic viewpoint, said marking targeting biopsy sub-module writes the position and orientation data to said data storage unit, and said data storage unit records the position and orientation data;
    when said marking targeting biopsy sub-module is operated to navigate the probe, said marking targeting biopsy sub-module reads the position and orientation data from said data storage unit and provides a guidance for the probe to a position and an orientation in the stomach cavity according to the position and orientation data.

9. The method of claim 6, wherein (a) through (g) take place during a first biopsy, and (h) takes place during a second biopsy.

* * * * *